United States Patent [19]
Strelow et al.

[11] Patent Number: 5,527,845
[45] Date of Patent: Jun. 18, 1996

[54] HOT MELT ADHESIVE COMPOSITION

[76] Inventors: Diane Strelow, W150 N11260 Montgomery Dr. No. 7, Germantown, Wis. 53022; Mark Alper, 3245 S. Pinewood Creek Ct. No. 105, New Berlin, Wis. 53151

[21] Appl. No.: 91,968

[22] Filed: Jul. 15, 1993

[51] Int. Cl.[6] .............................. C08K 5/52; C08K 5/09; C08L 33/08; B32B 7/12
[52] U.S. Cl. .................. 524/271; 524/143; 524/288; 524/292; 524/297; 428/349
[58] Field of Search .................... 524/271, 292, 524/297, 288, 143, 141; 428/349

[56] References Cited

U.S. PATENT DOCUMENTS

| | | | |
|---|---|---|---|
| 4,656,213 | 4/1987 | Schlademan | 524/272 |
| 4,937,138 | 6/1990 | Mostert | 428/349 |
| 5,024,888 | 6/1991 | Hwo et al. | 428/349 |
| 5,091,454 | 2/1992 | Arendt | 524/293 |

Primary Examiner—Paul R. Michl
Assistant Examiner—LaVonda R. DeWitt
Attorney, Agent, or Firm—Godfrey & Kahn

[57] ABSTRACT

A hot melt adhesive composition is described which possesses properties which are desirable with respect to the construction of disposable articles. The adhesive composition includes about 10% to about 80%, by weight, of an alkali soluble polymer; about 0 to about 30%, by weight, of a poly (vinyl methyl ether); about 30% to about 70%, by weight, of a tackifying resin; and about 5% to about 30%, by weight, of a suitable plasticizer.

7 Claims, No Drawings

HOT MELT ADHESIVE COMPOSITION

1. FIELD OF THE INVENTION

The present invention relates to hot melt adhesive compositions and more particularly, to a hot melt adhesive composition which finds utility in the manufacture of disposable soft goods such as diapers, feminine napkins and the like.

2. BACKGROUND OF THE INVENTION

The prior art is replete with numerous examples of hot melt adhesives which are employed for the construction of disposable soft goods. An example of a suitable hot melt adhesive for this purpose is disclosed in detail in U.S. Pat. No. 5,149,741 to Alper et al. Further, it is noted in that reference, that the prior art methods of application of these prior art adhesives have included, but are not limited to, extrusion [multi-bead or slot], spray or wheel application systems.

While the prior art hot melt adhesive compositions utilized heretofore have operated with varying degrees of success, they have several shortcomings which have detracted from their usefulness. For example, and while disposable garments such as incontinent briefs and disposable diapers have gained wide acceptance and are convenient and easy to utilize, concerns have been expressed regarding the environmental impact of such garments once they have become unserviceable or soiled and thereafter disposed of in landfills or the like.

As should be understood, no readily convenient method is now available for recycling, or otherwise separating the components of a nonwoven object of interest such as a disposable diaper into its component parts whereby the components may be recycled or alternatively disposed of in an environmentally friendly manner thus reducing any adverse impact these objects may have.

3. OBJECTS AND SUMMARY OF THE INVENTION

It is therefore the object of the present invention to provide an improved hot melt adhesive composition which is uniquely well suited for the manufacture of disposable soft goods.

It is a further object of the present invention to provide a hot melt adhesive composition which can be employed as either a single or multi-purpose adhesive and which further can be applied by utilizing either extrusion or spray techniques to at least one polyolefin substrate, and at least one elastic, polyolefin or nonwoven substrate thereby forming a laminate.

Another object of the present invention is to provide a hot melt adhesive which has the following composition:

(a) about 10% to about 80%, by weight, of an alkali soluble polymer;

(b) about 0 to about 30%, by weight, of a poly (vinyl methyl ether);

(c) about 30% to about 70%, by weight, of a tackifying resin;

(d) about 5% to about 30%, by weight, of a suitable plasticizer; and (e) about 0.1% to about 3%, by weight, of an antioxidant, and wherein the hot melt adhesive composition solubilizes when exposed to an aqueous solution having a pH greater than nine for a predetermined period of time.

Another object of the present invention is to provide a hot melt adhesive composition which can be employed in connection with the manufacture of disposable soft goods, and wherein the hot melt adhesive composition has an excellent dry bond strength but which can be induced to delaminate thereby permitting the component elements of the disposable soft good to be recycled or otherwise disposed of in an environmentally friendly manner.

Another object of the present invention is to provide a hot melt adhesive composition and wherein the alkali soluble polymer is selected from the group of polymers which include polyacrylate and polymethacrylate.

Another object of the present invention is to provide a hot melt adhesive composition which creates a bond which does not substantially degrade when exposed to water or urine, but which further readily solubilizes when exposed to a solution having a pH greater than nine (9) for a predetermined period of time.

Another object of the present invention is to provide a hot melt adhesive composition which has a viscosity of less than about 60,000 cP, and which further does not increase in viscosity or gel even under prolonged heat aging at normal application temperatures.

Another object of the present invention is to provide a hot melt adhesive composition which possesses an excellent balance of high specific adhesion, elevated temperature resistance and acceptable cohesive strengths at a relatively low viscosity.

Further objects and advantages of the present invention are to provide a hot melt adhesive composition for the purposes described, and which is durable, easy to apply, by utilizing conventional manufacturing techniques, and which further does not have the shortcomings attributable to the prior art adhesives utilized heretofore.

DESCRIPTION OF THE PREFERRED EMBODIMENT

The preferred adhesive composition of the present invention, as noted above includes, about 10% to about 80% by weight, of an alkali soluble polymer; about 0 to about 30%, by weight, of a poly (vinyl methyl ether); about 30% to about 70%, by weight, of a tackifying resin; about 5% to about 30%, by weight, of a suitable plasticizer, and about 0.1% to about 3%, by weight, of an antioxidant and wherein the hot melt adhesive composition solubilizes when exposed to a solution having a pH greater than nine (9) for a predetermined period.

The adhesive composition of the present invention includes, about 10% to about 80% by weight, of an alkali soluble polymer which is selected from the group which includes polyacrylates and polymethacrylates. Suitable alkali soluble polymers may be purchased commercially from Belland, Inc. of Andover, Mass. under the trade designation KBC 2026 SA; KBC 2180 SA and; KBC 4120 HA.

It will also be recognized that mixtures of the above identified polymers may also be utilized in the present formulations.

The hot melt adhesive composition of the present invention also includes, as noted above, about 0 to about 30%, by weight, of a poly (vinyl methyl ether) or other compatible polymer. This component of the adhesive composition is utilized to improve the characteristics of the adhesive with respect to rendering it suitable for spray applications as well as increasing the adhesive compositions tack and specific adhesion. The poly (vinyl methyl ether) can be purchased commercially from the Amoco Chemical Company of Chicago, Ill. under the trade designation "Amobond." In some applications, the poly (vinyl methyl ether) may not be necessary.

The present formulation includes about 30% to about 70% by weight of a tackifying resin which is selected from the group which includes polymerized rosin; partially hydrogenated rosin; terpene phenolics; and partial esters of dibasic modified tall oil rosin. Commercially available polymerized rosins may be secured from Arizona Chemical Company under the trade designations "Sylvatac 295, RX, R85, 95, and 140," respectively. Additionally, Hercules Chemical Company Inc. produces a suitable polymerized rosin under the trade designation "PolyPale Resin." Commercially suitable partially hydrogenated rosins may be secured from the Hercules Inc. under the trade designations "Foral AX" and "Stabelite." Commercially suitable terpene phenolics may be secured from the Arizona Chemical Company under the trade designations "Nirez V2040" and "V2150," respectively. Finally, partial esters of dibasic modified tall oil rosins may be secured from Arizona Chemical Company under the trade designation "Sylvatac 203," and "Beckacite 4901."

A plasticizer is present in the composition of the present invention in amounts of about 5% to about 30%, by weight. A suitable plasticizer may be selected from the group which includes dipropylene glycol dibenzoate; pentaerythritol tetrabenzoate; polyethylene glycol 400-di-2-ethylhexoate; 2-ethylhexyl diphenyl phosphate; and butyl benzyl phthalate. Suitable dipropylene glycol dibenzoate and pentaerythritol tetrabenzoate may be purchased from the Velsicol Chemical Company of Chicago, Ill. under the trade designations "Benzoflex 9-88 and S-552," respectively. Further, a suitable polyethylene glycol 400-di-2-ethylhexoate may be purchased from the C. P. Hall Company of Chicago, Ill. under the trade designation "Tegmer 809." Finally, a suitable 2-ethylhexyl diphenyl phosphate, and a butyl benzyl phthalate may be purchased from the Monsanto Industrial Chemical Company of St. Louis, Mo. under the trade designation "Santicizer 141 and 160," respectively.

The present invention may optionally include a stabilizer/antioxidant. The stabilizers which are useful in the hot melt adhesive compositions of the present invention are incorporated to help protect the polymers noted above, and thereby the total adhesive system, from the effects of thermal and oxidative degradation which normally occurs during the manufacture and application of the adhesive as well as in the ordinary exposure of the final assembled product to the ambient environment. Such degradation is usually manifested by a deterioration in the appearance, physical properties and performance characteristics of the adhesive. Among the applicable stabilizers are high molecular weight hindered phenols and multifunctional phenols, such as sulfur and phosphorous-containing phenols. Hindered phenols are well known to those skilled in the art and may be characterized as phenolic compounds which also contain sterically bulky radicals in close proximity to the phenolic hydroxyl group thereof. In particular, tertiary butyl groups generally are substituted onto the benzene ring in at least one of the ortho positions relative to the phenolic hydroxyl group. The presence of these sterically bulky substituted radicals in the vicinity of the hydroxyl group serves to retard its stretching frequency and correspondingly, its reactivity; this steric hindrance thus providing the phenolic compound with its stabilizing properties. Representative hindered phenols include:

1,3,5,-trimethyl-2,4,6-tris(3-5-ditert-butyl-4-hydroxybenzyl)benzene;

pentaerythritol tetrakis-3(3,5-di-tert-butyl-4-hydroxyphenyl)propionate;

n-octadecyl-3(3,5-di-tert-butyl-4-hydroxyphenyl)propionate;

4,4'-methylenebis(4-methyl-6-tert butylphenol);

4,4 '-thiobis(6-tert-butyl-o-cresol);

2,6-di-tert-butylphenol;

6-(4-hydroxyphenoxy)-2,4-bis(n-octylthio)-1,3,5-triazine;

di-n-octadecyl-3,5-di-tert-butyl-4-hydroxybenzylphosphonate;

2-(n-octylthio)ethyl-3,5-di-tert-butyl-4-hydroxybenzoate; and sorbitol hexa-(3,3,5-di-tert-butyl-4-hydroxy-phenyl)propionate].

Especially preferred as a stabilizer is pentaerythritol tetrakis-3(3,5-di-tert-butyl-4-hydroxyphenyl)propionate.

The performance of these stabilizers may be further enhanced by utilizing, in conjunction therewith; (1) synergists such as, for example, thiodipropionate esters and phosphites; and (2) chelating agents and metal deactivators as, for example, ethylenediaminetetraacetic acid, salts thereof, and disalicylalpropylenediimine. These stabilizers may be purchased from any one of the several chemical companies noted earlier.

The hot melt adhesive composition of the present invention may be formulated using any of the techniques known in the art. A representative example of the prior art procedure involves placing all of the substances, in a jacketed mixing kettle, and preferably in a jacketed heavy duty mixer of the Baker-Perkins or Day type, and which is equipped with rotors, and thereafter raising the temperature of this mixture to a range of about 250° F. to 350° F. It should be understood that the precise temperature to be used in this step would depend on the melting point of the particular ingredients. The resulting adhesive composition is agitated until the polymers completely dissolve. A vacuum is then applied to remove any entrapped air.

It should be understood that other optional additives may be incorporated into the adhesive composition of the present invention in order to modify particular physical properties. These may include, for example, such materials as colorants, or fillers.

The invention is further illustrated by way of the (nineteen) (19) examples which are set forth in TABLE I below. Each of the adhesive examples was manufactured by the general procedure described above. Further, each of the adhesive examples includes a suitable tackifying resin secured from Arizona Chemical Company under the trade designation "Sylvatec 295;" an alkali soluble polyacrylate polymer, which was secured from the Belland Chemical Company under the trade designation "KBC 2026 SA"; a poly (vinyl methyl ether) and which was secured from the Amoco Chemical Company under the trade designation "Amobond;" and a suitable plasticizer, which was secured from Velsicol Chemical Company under the trade designation "Benzoflex 9–88."

TABLE I

Examples

| No. | Constituent Elements (% by Weight) | | | | Physical Characteristics | | | | |
|---|---|---|---|---|---|---|---|---|---|
|  | 1 | 2 | 3 | 4 | 1 | 2 | 3 | 4 | 5 |
| 1: | 25 | 30 | 30 | 15 | 5225 | 180. | 10. | 1.5 | 78. |
| 2: | 65 | 10 | 10 | 15 | 358 | 141. | 8.5 | 1.5 | 38. |
| 3: | 25 | 30 | 25 | 20 | 3055 | 152. | 13. | 3. | 91. |
| 4: | 65 | 10 | 15 | 10 | 870 | 247. | 11. | 2. | 20. |
| 5: | 25 | 25 | 30 | 20 | 3430 | 144. | 15. | 3. | 105. |
| 6: | 65 | 15 | 10 | 10 | 660 | 91. | 17. | 1.5 | 8. |
| 7: | 60 | 10 | 10 | 20 | 348 | 144. | 12. | 2.5 | 100. |
| 8: | 50 | 10 | 30 | 10 | 2980 | 254. | 16. | 3. | 65. |
| 9: | 40 | 10 | 30 | 20 | 2063 | 146. | 18. | 2.5 | 135. |
| 10: | 40 | 30 | 10 | 20 | 885 | 140. | 12. | 3. | 123. |
| 11: | 60 | 11.67 | 18.33 | 10 | 1570 | 238. | 11. | 2. | 19. |
| 12: | 38 | 21 | 21 | 20 | 1638 | 127. | 12. | 3. | 118. |
| 13: | 57.5 | 16.25 | 10 | 16.25 | 680 | 124. | 15. | 2. | 53. |
| 14: | 35 | 18.75 | 30 | 16.25 | 4015 | 80. | 19. | 1.5 | 95. |
| 15: | 56 | 10 | 19 | 15 | 1465 | 162. | 15. | 2. | 65. |
| 16: | 30 | 30 | 21.67 | 18.33 | 3010 | 150. | 16. | 3. | 83. |
| 17: | 25 | 28.33 | 28.33 | 18.33 | 4605 | 152. | 16. | 1.5 | 76. |
| 18: | 65 | 11.67 | 11.67 | 11.67 | 680 | 294. | 17. | 3. | 12. |
| 19: | 46 | 18 | 20 | 16 | 1500 | 182. | 19. | 3. | 96. |

Constituent Elements:
1.) Tackifying Resin (Arizona Chemical Co. "Sylvatac 295").
2.) Alkali Soluable Polyacrylate Polymer; (Belland Chemical Co. "KBC 2026").
3.) Poly (Vinyl Methyl Ether); (Amoco Chemical Corp. "Amobond").
4.) Plasticizer; (Velsicol Chemical Co., "Benzoflex 988).

Physical Characteristics:
1.) Viscosity; (expressed in cP at 325° F.).
2.) Dry Peel Strength; (expressed in grams).
3.) Wet Peel Strength; (expressed in grams).
4.) Suitability when spiral sprayed; expressed as a scale with 1 being poor, and 3 being excellent).
5.) Hardness; (expressed in decimillimeters).

Following the formulation of each of the adhesive composition examples which are summarized above, each of the examples were tested with respect to viscosity; hardness; dry peel strength; and wet peel strength. In this regard, wet peel strength was determined following a five (5) minute soak in an aqueous solution which contained 1% ammonium hydroxide (NH₄OH) and which had a pH of approximately eleven (11). The tests further included a determination of the suitability of the same adhesive when spiral sprayed. The spraying test results are expressed as a scale with an unsuitable spray pattern being expressed as a 1, and an excellent pattern being expressed as a 3. Viscosity was measured by employing conventional technology. More particularly, the viscosity of each of the adhesive formulation examples was measured at a temperature of 325° F., and is expressed herein in Centipoise [cP]. A Brookfield Thermosel was utilized to determine the viscosity. The viscosity measurements were done in accordance with ASTM method D 3236-73.

The hardness of each of the adhesive samples, noted above, were determined. In summary, each of the adhesive samples were exposed to a needle which has a 200 gram load applied thereto. The needle and the associated 200 gram load are placed on the surface of each of the adhesives and then permitted to free fall during the test for a period of approximately five seconds. Hardness is then expressed as the depth of penetration of the needle expressed in decimilimeters (dmm). As noted above, the suitability of the respective adhesive compositions for use in spray applications is determined by visually inspecting laminates following application of the individual adhesives using typical spray application equipment. Following spraying, the pattern of the adhesive is visually inspected and awarded a relative value on the scale, as described above. With respect to the dry peel and wet peel bond strength tests, it should be understood that the laminates were prepared and which include a polyethylene back sheet upon which is applied the adhesive candidate to be tested. In particular, one spiral sprayhead was mounted on an Acumeter LH-1 Coater. Each of the adhesive composition examples were then extruded at a temperature of 300° F. through a 0.018 inch nozzle. The adhesive compositions were each sprayed onto the polyethylene substrate to an amount equal to about 3.0 mg. per square inch. During the process, an air temperature of approximately 400° F. was employed. After an open time of approximately 0.5 seconds, the polyethylene sheet was pressed into contact with a nonwoven substrate to form a laminate. Following preparation of the laminates by means of the process outlined, above, samples of the laminates were tested for their dry peel bond strength by subjecting each of the laminates to a 180° peel with an Instron tensile tester at a cross head speed of approximately 12 inches per minute. Other samples of the same laminates are then submerged for five (5) minutes in a 1% ammonium hydroxide (NH₄OH) solution. Following submersion for five minutes, the selected laminates are removed and are immediately subjected to a 180° peel to determine the wet peel bond strength at the same speed of approximately 12 inches per minute.

An analysis of the test results, noted above, demonstrate that the adhesive compositions of the present invention provide unusually desirable characteristics when combined with a nonwoven, and polyethylene substrate to form disposable soft goods. For example, it should be recognized that the adhesive composition of the present invention produces desirable viscosities, that is, viscosities that are less than 60,000 cP as measured at 325° F. thereby permitting it to be utilized with all the prior art application methods. Additionally, the present adhesive formulation in the dry peel test demonstrates sufficient bond strength to make it suitable as a construction type adhesive for nonwoven garments and the like. The test results are further surprising in view of wet peel strength of the adhesive formulations. More specifically, a review of the test results demonstrate that the strength of the adhesive bond rapidly degrades to the point of being insignificant when exposed to an aqueous alkaline solution as disclosed above. In addition to the foregoing the hardness, and spray characteristics of the adhesive are acceptable by industry standards.

These test results demonstrate that the adhesive composition of the present invention can be utilized as an adhesive for manufacturing a laminate that may be a component part of a nonwoven garment, but which further, when exposed to an aqueous alkaline solution readily degrades thereby permitting the component portions of the laminate to be separated, one from the other, for purposes of recycling, disposal, or the like. In contrast to these test results, a typical hot melt adhesive composition such as what is disclosed in the Alper U.S. Pat. No. 5,149,741 does not readily solubilize or change with respect to its bond strength following exposure to a similar alkali solution.

To further demonstrate the novel characteristics of the new adhesive composition, adhesives compounded in accordance with the techniques noted above, and having the formulations as noted in Examples 8 and 19, above, were compared and contrasted with a dry control following submersion for five (5) minutes in the solutions as set forth in Table II below.

TABLE II

| Soaking Solution | Example 8 Peel (gm) | Example 8 Notes | Example 19 Peel (gm) | Example 19 Notes |
| --- | --- | --- | --- | --- |
| Dry (Control) | 254 | Polyethylene Distortion | 182 | Polyethylene Distortion |
| Synthetic Urine (pH 6.0) | 275 | Polyethylene Distortion | 175 | Polyethylene Distortion |
| Tap Water (PH 7.5) | 274 | Polyethylene Distortion | 196 | Polyethylene Distortion |
| 1% NH₄OH (PH 11.5) | 10 | Totally Solubilized | 14 | Totally Solubilized |
| 0.5% NH₄OH | 13 | Totally Solubilized | 9.3 | Totally Solubilized |
| 0.1% NH₄OH | 22 | Slight Adhesion | 15 | Slight Adhesion |
| 1% NaOH (PH 13) | 14 | Totally Solubilized | 14 | Totally Solubilized |
| NaCO3 | 30 | Slight Adhesion | 18 | Slight Adhesion |

In these tests, laminates were prepared in a fashion similar to that which was earlier discussed, that is, the adhesive compositions were spiral sprayed onto a polyethylene sheet in an amount equal to approximately 3 mg. per square inch. Following an open time of approximately 0.5 seconds, the polyethylene sheet was combined with a nonwoven substrate. The adhesive was applied at a temperature of approximately 300° F., and the air stream temperature utilized in connection with spraying the adhesive was approximately 400° F. The polyethylene and the nonwoven laminates were submerged in the designated solutions and then immediately removed and subjected to a 180° peel by utilizing an Instron Tensile tester, as earlier discussed, utilizing a cross head speed of approximately 12 inches per minute.

The test results, above, demonstrate that the bond strength of the adhesive of the present invention is unaffected when exposed to synthetic urine and tap water, these individual cohesive strengths being substantially identical to that of the dry control. In particular, the test results indicate that in each instance, the strength of the adhesive bond was sufficient to cause polyethylene distortion when the laminates were exposed to the cross head speed of 12 inches per minute. This retention of bond strength suggests that disposable soft goods manufactured with adhesives of the present invention would not fail during normal use, as for example, when used in constructing a diaper, but would only weaken, and solubilize, when exposed to an appropriate alkaline solution. The test results further demonstrate that the adhesive composition of the present invention rapidly degrades when exposed to an alkaline solution such as the solutions indicated in the chart noted above, and more specifically, 1%, 0.5% and 0.1% ammonium hydroxide [NH₄OH]; 1% sodium hydroxide [NaOH]; and 1% sodium carbonate (NaCo₃). Further, and in both examples noted above, a 1% solution of ammonium hydroxide caused the adhesive bond to become totally solubilized. Similar results were achieved when the adhesive bond was exposed to the 0.5% ammonium hydroxide solution. The test results further demonstrate that the solutions, including 0.1% ammonium hydroxide, 1% sodium hydroxide and 1% sodium carbonate degraded the adhesive bond sufficiently such that the laminates could be separated for disposal, recycling, or the like.

In summary, therefore, it will be noted that the adhesive compositions of the present invention provide a fully dependable and practical means for adhesively assembling a disposable soft good such as a disposable diaper, feminine napkin and the like, and which further avoids the detriments associated with the prior art practices which includes, among others, employing an adhesive which inhibits the disassembly of the garment following its utilization for purposes of recycling, disposal or the like. Further the adhesives of the present invention are unaffected when exposed to urine or tap water, but readily degrade and become solubilized following exposure to an alkaline solution thereby permitting the garment to be disassembled. In addition to the foregoing, the improved hot melt adhesive composition of the present invention shows surprising and unusually desirable manufacturing viscosities when compared with the prior art, and bond strengths which are comparable to those achieved by the prior art.

It will be apparent to those skilled in the art that the foregoing examples have been made for purposes of illustration and that variations may be made in proportions, procedures and material without departing from the scope of the present invention. Therefore, it is intended that this invention not be limited except by the claims which follow:

Having described our new invention, what we claim as new and desire to secure by Letters Patent of the United States is:

1. A hot melt adhesive composition comprising:
   about 10% to about 80%, by weight, of an alkali soluble polymer, and wherein the alkali soluble polymer is selected from the group consisting of polyacrylate and polymethacrylate;
   about 0 to about 30%, by weight, of a poly (vinyl methyl ether);
   about 30% to about 70%, by weight, of a tackifying resin;
   about 5% to about 30%, by weight, of a plasticizer, and wherein the plasticizer is selected from the group consisting of dipropylene glycol dibenzoate, pentaerythritol tetrabenzoate; polyethylene glycol 400-di-2-ethyl hexoate; 2-ethylhexyl diphenyl phosphate; and butyl benzyl phthalate; and
   about 0.1% to about 3%, by weight, of an antioxidant, and wherein the adhesive is operable to bind a polyolefin or nonwoven substrate to at least one elastic polyolefin, foam, or nonwoven substrate to form a laminate, and wherein the adhesive when exposed to an aqueous solution which has a pH of 7.5 or greater solubilizes to a degree which permits the laminate to separate into its component parts.

2. A hot melt adhesive composition as claimed in claim 1, and wherein the aqueous solution is selected from the group of solutions consisting of NH₄OH; NaOH, and NaCo₃; and wherein the adhesive further has a viscosity of less than about 60,000 cP at 325° F.

3. A hot melt adhesive composition as claimed in claim 2 and wherein the adhesive composition has a dry peel strength of greater than 80 grams and a wet peel strength, following exposure to the solution for a period of about five minutes duration of less than about 20 grams.

4. A hot melt adhesive composition as claimed in claim 3, and wherein the tackifying resin is selected from the group of tackifying resins consisting of polymerized rosin, partially hydrogenated rosin; terpene phenolics and partial esteres of dibasic modified tall oil rosin.

5. A hot melt adhesive composition comprising:
   about 40%, by weight, of an alkali soluble polymer;
   about 45%, by weight, of a tackifying resin;
   about 15%, by weight, of a plasticizer; and
   about 1%, by weight, of an antioxidant, and wherein the adhesive is operable to bind a polyolefin or nonwoven substrate to at least one elastic polyolefin, foam, or nonwoven substrate to form a laminate, and wherein the hot melt adhesive composition when exposed to an aqueous solution having a pH of 7.5 or greater solubilizes to a degree which permits the laminate to separate into its component parts, and further has a dry peel strength of greater than 80 grams and a wet peel strength following exposure to the aqueous solution of about 5 minutes duration of less than 20 grams.

6. A hot melt adhesive comprising:

about 20%, by weight, of an alkali soluble polymer;

about 20%, by weight, of a poly (vinyl methyl ether);

about 45%, by weight, of a tackifying resin;

about 15%, by weight, of a plasticizer; and about 1%, by weight, of an antioxidant, and wherein the hot melt adhesive composition is operable to bind a polyolefin or nonwoven substrate to at least one elastic, polyolefin, foam or nonwoven substrate to form a laminate, and wherein the hot melt adhesive composition when exposed to an aqueous solution having a pH of 7.5 or greater solubilizes to a degree which permits the laminate to separate into its component parts, and wherein the adhesive composition has a dry peel strength of greater than 80 grams, and a wet peel strength, following exposure to the aqueous solution for a period of about 5 minutes of less than 20 grams.

7. A hot melt adhesive composition comprising:

about 10% to about 80%, by weight, of an alkali soluble polymer;

about 0% to about 30%, by weight, of a poly (vinyl methyl ether);

about 30% to about 70%, by weight, of a tackifying resin;

about 5% to about 30%, by weight, of a plasticizer; and about 1% to about 3%, by weight, of an antioxidant and wherein the hot melt adhesive composition is operable to bind a polyolefin, or nonwoven substrate to at least one elastic, polyolefin, foam, or nonwoven substrate to form a laminate, and wherein the hot melt adhesive composition when exposed to an aqueous solution having a pH of 7.5 or greater solubilizes to a degree which permits the laminate to separate into its component parts, and wherein, further the adhesive composition has a viscosity of less than about 60,000 cP at 325° F. and a dry peel strength of greater than 80 grams, and a wet peel strength following exposure to the aqueous solution for about 5 minutes of less than about 20 grams.

* * * * *